(12) United States Patent
Lin et al.

(10) Patent No.: US 12,245,872 B2
(45) Date of Patent: Mar. 11, 2025

(54) ELECTRONIC DEVICE

(71) Applicant: Advanced Semiconductor Engineering, Inc., Kaohsiung (TW)

(72) Inventors: Chih Lung Lin, Kaohsiung (TW); Kuei-Hao Tseng, Kaohsiung (TW); Te Kao Tsui, Kaohsiung (TW); Kai Hung Wang, Kaohsiung (TW); Hung-I Lin, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 513 days.

(21) Appl. No.: 17/244,876

(22) Filed: Apr. 29, 2021

(65) Prior Publication Data

US 2022/0346715 A1  Nov. 3, 2022

(51) Int. Cl.
| | | |
|---|---|---|
| *A61B 5/00* | (2006.01) | |
| *H05K 1/02* | (2006.01) | |
| *A61B 5/024* | (2006.01) | |
| *A61B 5/0531* | (2021.01) | |
| *A61B 5/145* | (2006.01) | |
| *A61B 5/318* | (2021.01) | |
| *A61B 5/369* | (2021.01) | |
| *A61B 5/389* | (2021.01) | |
| *A61B 5/398* | (2021.01) | |

(52) U.S. Cl.
CPC .......... *A61B 5/6817* (2013.01); *A61B 5/0002* (2013.01); *H05K 1/0277* (2013.01); *A61B 5/024* (2013.01); *A61B 5/02405* (2013.01); *A61B 5/0531* (2013.01); *A61B 5/14517* (2013.01); *A61B 5/14539* (2013.01); *A61B 5/318* (2021.01); *A61B 5/369* (2021.01); *A61B 5/389* (2021.01); *A61B 5/398* (2021.01); *A61B 2562/0204* (2013.01); *A61B 2562/0209* (2013.01); *A61B 2562/0219* (2013.01); *A61B 2562/0238* (2013.01); *A61B 2562/0247* (2013.01); *A61B 2562/0271* (2013.01); *A61B 2562/029* (2013.01); *A61B 2562/12* (2013.01); *A61B 2562/164* (2013.01); *H05K 2201/10151* (2013.01)

(58) Field of Classification Search
CPC ..................... H05K 1/0277; H05K 220/10151
See application file for complete search history.

(56) References Cited

U.S. PATENT DOCUMENTS

| | | | | |
|---|---|---|---|---|
| 2009/0088611 | A1* | 4/2009 | Buschmann | A61B 5/00 600/301 |
| 2019/0045291 | A1* | 2/2019 | Kofman | A61B 5/0075 |
| 2019/0246982 | A1* | 8/2019 | Mackellar | A61M 21/00 |

(Continued)

OTHER PUBLICATIONS

U.S. Appl. No. 16/823,074, filed Mar. 18, 2020, Huang et al.

*Primary Examiner* — Mallika D Fairchild
*Assistant Examiner* — Thien Jason Tran
(74) *Attorney, Agent, or Firm* — FOLEY & LARDNER LLP

(57) ABSTRACT

The present disclosure provides an electronic device. The electronic device includes a flexible element, and a sensing element adjacent to the flexible element and configured to detect a biosignal. The electronic device also includes an active component in the flexible element and electrically connected with the sensing element. A method of manufacturing an electronic device is also disclosed.

2 Claims, 17 Drawing Sheets

(56) References Cited

U.S. PATENT DOCUMENTS

| | | | | |
|---|---|---|---|---|
| 2020/0359921 A1* | 11/2020 | Manoli | ................. | A61B 5/302 |
| 2021/0137457 A1* | 5/2021 | Matsumoto | .......... | A61B 5/4266 |
| 2021/0152924 A1* | 5/2021 | Keady | ................. | H04R 1/1083 |
| 2021/0297765 A1* | 9/2021 | Huang | ................... | A61B 5/256 |
| 2022/0104769 A1* | 4/2022 | Baba | .................... | H04R 1/1025 |

* cited by examiner

ELECTRONIC DEVICE

BACKGROUND

1. Technical Field

The present disclosure relates to an electronic device and method of manufacturing an electronic device.

2. Description of the Related Art

Numerous methods have been developed to obtain information or signals reflecting physical activity and/or health through non-invasive subject measurements. For example, sensors may be integrated into wearable devices or swallowed capsules to achieve the desired sensing ability.

However, physical considerations (for example, size and/or weight required to perform the required detection) can present challenges. Furthermore, such measurements may suffer from low signal-to-noise ratio (SNR) since signals obtained are typically weak in comparison to background noise or because of signal attenuation during transmission.

SUMMARY

In some embodiments, an electronic device includes a flexible element, and a sensing element adjacent to the flexible element and configured to detect a biosignal. The electronic device also includes an active component in the flexible element and electrically connected with the sensing element.

In some embodiments, an electronic device includes a flexible element, a sensing element, and a component configured to receive a signal from the sensing element. The component is configured to process the signal within the flexible element.

In some embodiments, a method of manufacturing an electronic device includes providing a sensing element, providing a component configured to receive a signal from the sensing element, and integrating the sensing element and the component into a flexible element.

BRIEF DESCRIPTION OF THE DRAWINGS

Aspects of some embodiments of the present disclosure are best understood from the following detailed description when read with the accompanying figures. It is noted that various structures may not be drawn to scale, and dimensions of the various structures may be arbitrarily increased or reduced for clarity of discussion.

DETAILED DESCRIPTION

Figure 1A:
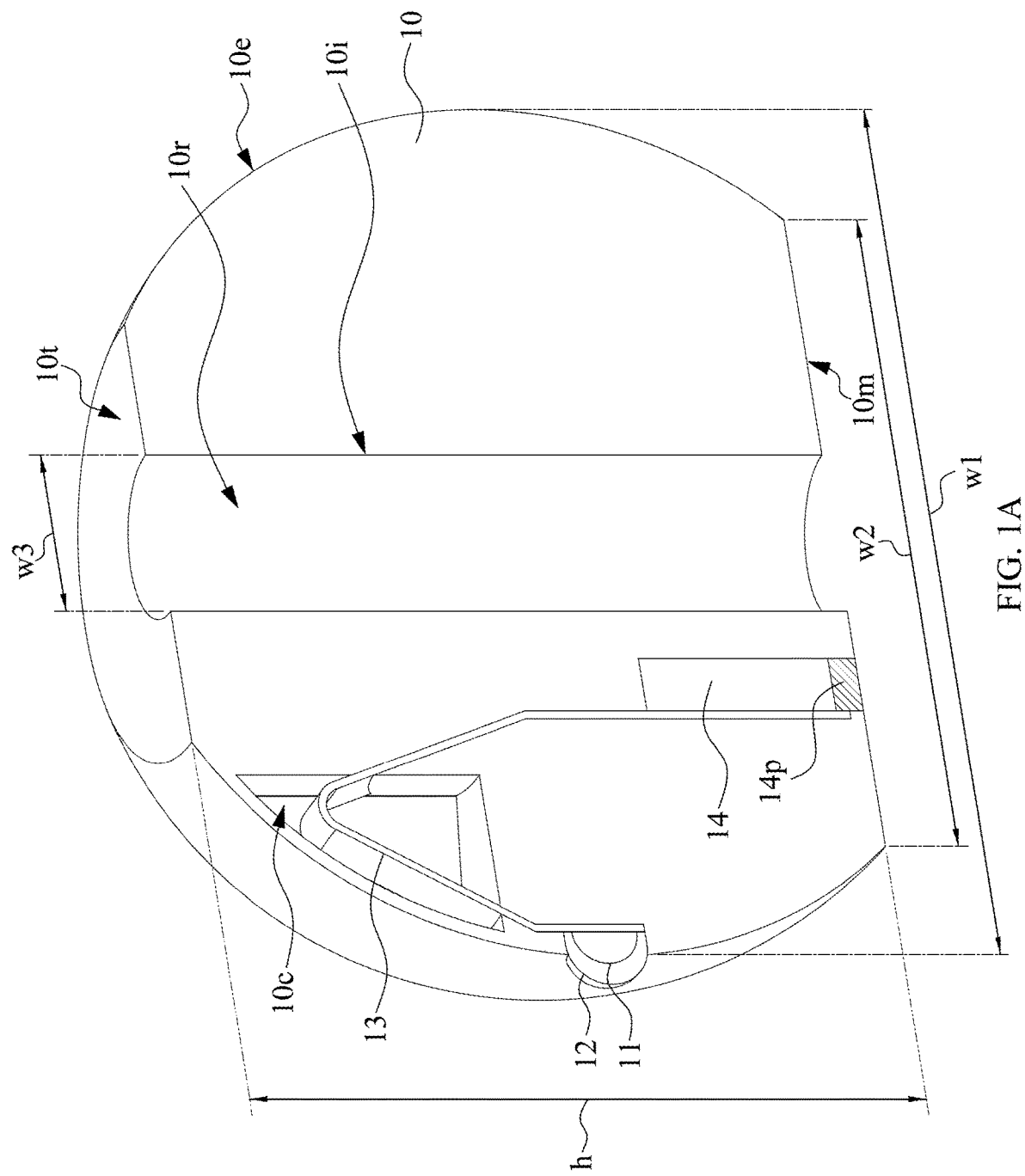
FIG. 1A illustrates a cross-sectional view of an electronic device in accordance with some embodiments of the present disclosure.

The following disclosure provides for many different embodiments, or examples, for implementing different features of the provided subject matter. Specific examples of components and arrangements are described as follows to explain certain aspects of the present disclosure. These are, of course, merely examples and are not intended to be limiting. For example, the formation of a first feature over or on a second feature in the description that follows may include embodiments in which the first and second features are formed or disposed in direct contact, and may also include embodiments in which additional features may be formed or disposed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Spatial descriptions, such as "above," "below," "up," "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of embodiments of this disclosure are not deviated from by such arrangement.

The following description involves an electronic device and method of manufacturing an electronic device.

FIG. 1A illustrates a cross-sectional view of an electronic device 1 in accordance with some embodiments of the present disclosure. The electronic device 1 may include an ear tip of an earpiece. Application or usage of the electronic device 1 in the figures is for illustrative purposes only, and not intended to limit the present disclosure. The electronic device 1 of the present disclosure can be used in combination with any wearable device, for example, in some embodiments, equipment that transmits audio signals. In some embodiments, electronic device 1 can be used in combination with a detection device, an electronic device (such as a signal processing device) and/or other corresponding external device for further processing acquired signals.

In some embodiments, the electronic device 1 of the present disclosure may be edible. For example, the electronic device 1 of the present disclosure may be safe or suitable to eat. For example, in some embodiments, the electronic device 1 of the present disclosure may be used in combination with a capsule (a swallowed capsule) or other consumable configuration.

As shown in FIG. 1A, the electronic device 1 may have a flexible element 10, a sensing element (or detection element) 11, a protection layer 12, a connector 13, and an active component 14.

The flexible element 10 may have a top side 10t and a bottom side 10m opposite to the top side 10t. In some embodiments, when the electronic device 1 is worn by a user, the top side 10t of the flexible element 10 sits more deeply into (or extends further into) the user's ear canal than does the bottom side 10m. The electronic device 1 may have a height (annotated as "h" in FIG. 1A) measured between the top side 10t and the bottom side 10m. In some embodiments, the height h of the flexible element 10 may be between about 8 millimeters (mm) and about 12 mm. For example, the height h of the flexible element 10 may be between about 9 mm and about 11 mm. For example, the height h of the flexible element 10 may be about 10 mm.

The flexible element 10 may have an external surface 10e and an internal surface 10i opposite to the external surface 10e. The external surface 10e of the flexible element 10 may define an outside diameter. The internal surface 10i of the flexible element 10 may define an inside diameter. When the electronic device 1 is worn by a user, the external surface 10e of the flexible element 10 may be in contact with the user, and the internal surface 10i of the flexible element 10 may be spaced apart from the user. The internal surface 10i of the flexible element 10 may define a space 10r for receiving another piece of equipment (such as a sound hole 15a of a piece of equipment 15 illustrated in FIG. 1C).

The external surface 10e may define the greatest width or the greatest outside diameter (annotated as "w1" in FIG. 1A) of the electronic device 1. The external surface 10e may define the smallest width or the smallest outside diameter (annotated as "w2" in FIG. 1A) of the electronic device 1. In some embodiments, a width or an outside diameter (including the greatest outside diameter w1 and the smallest outside diameter w2) of the flexible element 10 may be between about 6 mm and about 12 mm. For example, a width or an outside diameter of the flexible element 10 may be between about 7 mm and about 11 mm. For example, a width or an outside diameter of the flexible element 10 may be between about 8 mm and about 10 mm.

The internal surface 10i may define an inside diameter (annotated as "w3" in FIG. 1A) of the electronic device 1. In some embodiments, a width or an inside diameter w3 may be between about 1 mm and about 3 mm, such as about 2 mm.

In some embodiments, the flexible element 10 may include, for example, rubber, silicon, sponge, or other suitable materials such as an elastic material, a soft material, or a flexible material. In some embodiments, the flexible element 10 may include a liquid silicone rubber (LSR).

The flexible element 10 may be soft and flexible enough for the user to wear comfortably for an extended time period. In some embodiments, the flexible element 10 may have material(s) which can resist relatively more stress, impact, twisting or other physical or structural changes. For example, the flexible element 10 may be resilient, such that, after being squeezed or deformed, it can return to its original state. In some embodiments, when the electronic device 1 is worn, the flexible element 10 may be conformal to the user's ear canal. In some embodiments, the carrier 10 may flexibly adjust its shape to conform to the user's ear canal. In some embodiments, the carrier 10 may flexibly adjust its shape to conform to other body parts of the user.

In some embodiments, the flexible element 10 may be water-resistant, water-repellent, or waterproof. In some embodiments, the flexible element 10 may be acid-resistant, acid-repellent, or acid-proof. In some embodiments, the material of the flexible element 10 may be chosen based on other requirements such as sound quality, impermeability, a skin-friendly property (such as hypoallergenicity), etc.

In some embodiments, the flexible element 10 may define a cavity 10c. In some embodiments, the cavity 10c may not be exposed by the flexible element 10. For example, the cavity 10c may be disposed between the top side 10t and the bottom side 10m. For example, the cavity 10c may be disposed between the external surface 10e and the internal surface 10i. For example, the cavity 10c may be surrounded by the flexible element 10. For example, the cavity 10c may be within the flexible element 10 such that the flexible element 10 is hollow. In some embodiments, the cavity 10c may be an empty space defined by the flexible element 10. For example, the cavity 10c may be filled with air. In some embodiments, the cavity 10c may be filled with one or more materials different from the flexible element 10.

A portion of the connector 13 may be located within the cavity 10c. For example, a portion of the connector 13 may be exposed by the flexible element 10. For example, the connector 13 may have one end connected to the sensing element 11, another end connected to the active component 14, and a portion of the connector 13 between the two ends may be located within the cavity 10c.

In some embodiments, the cavity 10c may function as a buffer for the connector 13. For example, when the flexible element 10 is squeezed or deformed, stress concentrations may occur on the connector 13, such as on the interface between the connector 13 and the flexible element 10. The cavity 10c may help release or reduce the stress of the flexible element 10 on the connector 13. For example, the connector 13 may release the stress in the cavity 10c which prevents it from breaking. Therefore, the reliability of the electronic device 1 may be enhanced.

The sensing element 11 may be surrounded, embedded, or covered by the flexible element 10. The sensing element 11 may be surrounded, embedded, or covered by the protection layer 12. In some embodiments, as shown in FIG. 1A, the sensing element 11 is partially embedded in the flexible element 10, and partially embedded in the protection layer 12. However, in some embodiments, the sensing element 11 may be entirely embedded in the flexible element 10. In some embodiments, as shown in FIG. 1A, the sensing element 11 protrudes from the external surface 10e of the flexible element 10. However, in some embodiments, the sensing element 11 may not protrude from the external surface 10e of the flexible element 10. The sensing element 11 may be adjacent to the protection layer 12. The sensing element 11 may be adjacent to the flexible element 10. The sensing element 11 may be adjacent to the external surface 10e of the flexible element 10.

In some embodiments, the sensing element 11 may be an electrode, a thermistor, a pressure sensor, a proximity sensor, a motion sensor, an acoustic sensor, a smell sensor, a particle sensor, a humidity sensor, an optical transmitter, an optical receiver, an optical transceiver, or a combination thereof.

In some embodiments, the sensing element 11 may be used to detect or collect one or more information or signals external to the electronic device 1. For example, the sensing element 11 may be used to detect one or more signals from the surroundings of the electronic device 1. For example, the sensing element 11 may be used to detect temperature, air pressure, smell, particle, sound, light, humidity, or other environmental variables. For example, the sensing element 11 may be used to detect one or more signals associated with the user of the electronic device 1. For example, the sensing element 11 may be used to detect one or more biosignals of the user. For example, the biosignal detected by the sensing element 11 may be further processed by the active component 14 to determine a biological parameter of the user, such as a pulse travel time (PTT), an electroencephalogram (EEG), electrocardiogram (ECG), electromyogram (EMG), electrooculogram (EOG), galvanic skin response (GSR), sweat composition, pH, heart rate variability (HRV), or other biologically-relevant information associated with the user.

The positions, the functions, and the numbers of the sensing elements in the electronic device 1 are not intended to limit the present disclosure. For example, there may be any number of sensing elements in the electronic device 1 due to design requirements. For example, as shown in FIG. 5, the electronic device 5 may further include a sensing element 50 different from the sensing element 11 (which will be further described with respect to FIG. 5).

In some embodiments, the protection layer 12 may be disposed on the external surface 10e of the flexible element 10. In some embodiments, the protection layer 12 may cover the sensing element 11. For example, the protection layer 12 may cover an exposed portion of the sensing element 11. In some embodiments, the protection layer 12 may be configured to protect the sensing element 11.

In some embodiments, as shown in FIG. 1A, the protection layer 12 protrudes from the external surface 10e of the flexible element 10. However, in some embodiments, the protection layer 12 may not protrude from the external surface 10e of the flexible element 10. For example, the protection layer 12 may be substantially coplanar with the external surface 10e of the flexible element 10.

In some embodiments, the protection layer 12 may include a material as listed previously for the flexible element 10. In some embodiments, the protection layer 12 may have a characteristic or property as listed previously for the flexible element 10. In some embodiments, the material of the protection layer 12 may be chosen based on the functions of the sensing element 11. For example, if the sensing element 11 includes an electrode, the protection layer 12 may have a relatively low impedance, such as an ultra-low impedance. For example, if the sensing element 11 includes a thermistor, the protection layer 12 may have a relatively high thermal conductivity. For example, if the sensing element 11 includes an optical sensor (such as an optical transmitter, an optical receiver, or an optical transceiver), the protection layer 12 may have a standard optical transparency.

In some embodiments, the protection layer 12 and the flexible element 10 may have the same material. In some embodiments, the protection layer 12 and the flexible element 10 may have different materials. In some embodiments, the interface between the protection layer 12 and the flexible element 10 may be observable. In some embodiments, there may be no existing interface between the protection layer 12 and the flexible element 10.

The sensing element 11 may be electrically connected to the active component 14 for signal transmission. For example, the sensing element 11 may be electrically connected to the active component 14 through the connector 13.

In some embodiments, the connector 13 may include a flexible printed circuit (FPC), a conductive wire, a redistribution layer (RDL), or a combination thereof. The sensing element 11 may be connected to the active component 14 by using another alternative method(s) or component(s). For example, the sensing element 11 may be connected to the active component 14 by using any bridged element.

In some embodiments, the connector 13 may be disposed within the flexible element 10. For example, the connector 13 may be disposed between the top side 10t and the bottom side 10m. For example, the connector 13 may be disposed between the external surface 10e and the internal surface 10i. For example, the connector 13 may be disposed between the sensing element 11 and the active component 14. For example, the connector 13 may be surrounded by the flexible element 10. In some embodiments, as shown in FIG. 1A, the connector 13 is partially encapsulated in the flexible element 10 and a portion of the connector 13 is within the cavity 10c. For example, a portion of the connector 13 is exposed by the flexible element 10. For example, a portion of the connector 13 is exposed to air.

In some embodiments, the active component 14 includes a system-in-package (SiP). In some embodiments, the active component 14 may include a data conversion component, a processing component, a storage component, a transmission component, or a combination thereof. In some embodiments, the active component 14 may include an analog-to-digital converter.

In some embodiments, the active component 14 may be configured to receive a signal through the connector 13 from the sensing element 11. In some embodiments, the signal may be from a biosignal detected by the sensing element 11. In some embodiments, the active component 14 may be configured to receive the signal from the sensing element 11. In some embodiments, the active component 14 may be configured to process the signal from the sensing element 11. In some embodiments, the signal may be an analog signal and may be converted to a digital signal by the active component 14. In some embodiments, the signal may be amplified by the active component 14. In some embodiments, the signal may be stored by the active component 14. In some embodiments, the active component 14 may be configured to receive the signal from the sensing element 11 through wireless communication.

In some embodiments, the signal transmission or a signal path between the sensing element 11 and the active component 14 may be within the flexible element 10. For example, the signal transmission or a signal path between the sensing element 11 and the active component 14 may be disposed between the top side 10t and the bottom side 10m. For example, the signal transmission or a signal path between the sensing element 11 and the active component 14 may be disposed between the external surface 10e and the internal surface 10i. For example, the signal transmission or a signal path between the sensing element 11 and the active component 14 may be surrounded by the flexible element 10. For example, the signal transmission or a signal path between the sensing element 11 and the active component 14 may be entirely within the flexible element 10.

In some embodiments, the signal from the sensing element 11 may be converted to a digital signal (such as by the active component 14) within the flexible element 10. In some embodiments, the signal from the sensing element 11 may be amplified (such as by the active component 14) within the flexible element 10. In some embodiments, the signal from the sensing element 11 may be stored (such as by the active component 14) within the flexible element 10.

In some embodiments, since the active component 14 and the sensing element 11 are incorporated in the flexible element 10, the biosignal detected by the sensing element 11 can be processed (e.g., converted to a digital signal, amplified, stored, etc.) within the flexible element 10. Therefore, the signal noise can be reduced, and the electronic device 1 can provide high dynamic range signal digitization. In addition, the overall circuit in the electronic device 1 can consume less power and occupy a smaller area.

In some embodiments, the active component 14 may transmit the processed signal or the signal to an external device. For example, the active component 14 may be disposed adjacent to the bottom side 10m of the flexible element 10, and a conductive element 14p (such as a conductive pin of the active component 14) may be at least partially exposed by the bottom side 10m of the flexible element 10. For example, a conductive pin of the active component 14 may be at least partially exposed by the bottom side 10m of the flexible element 10. The conductive element 14p may provide electrical connections between the electronic device 1 and external components (e.g., external circuits or circuit boards).

Figure 1B:
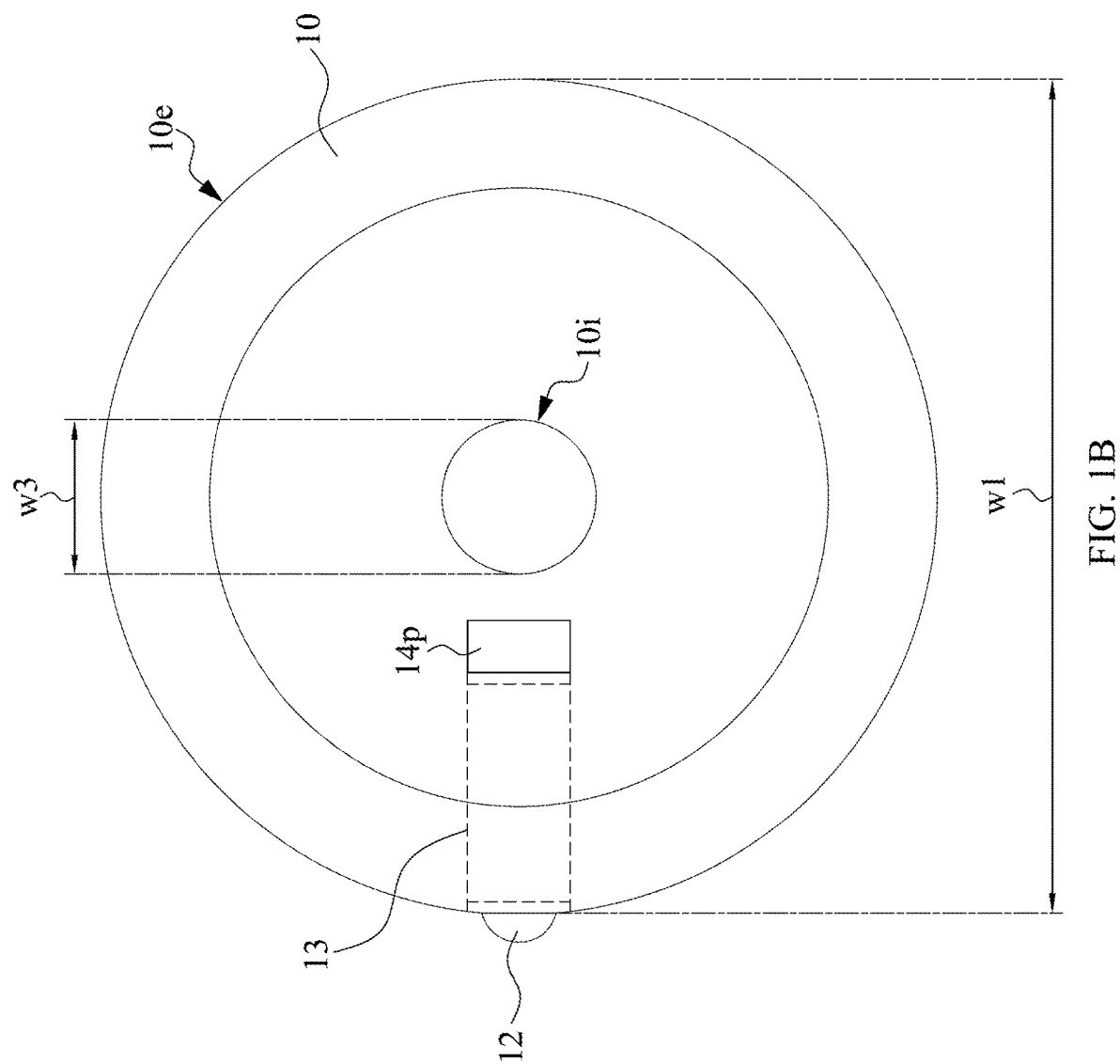
FIG. 1B illustrates a bottom view of an electronic device in accordance with some embodiments of the present disclosure.

FIG. 1B illustrates a bottom view of an electronic device in accordance with some embodiments of the present disclosure. In some embodiments, the bottom view in FIG. 1B may be a bottom view of the electronic device 1 in FIG. 1A. It should be noted that only the flexible element 10, the protection layer 12, the connector 13, and the conductive element 14p are illustrated in FIG. 1B, and some components of the electronic device 1 in FIG. 1A are omitted for conciseness.

As shown in FIG. 1B, the conductive element 14p is at least partially exposed by the flexible element 10. The dashed line is illustrated to present a contour of the connector 13. From the bottom view, the connector 13 may be located between the external surface 10e and the internal surface 10i. For example, the connector 13 may be located between the outside diameter (which is defined by the external surface 10e) and the inside diameter of the flexible element 10 (which is defined by the internal surface 10i).

Figure 1C:
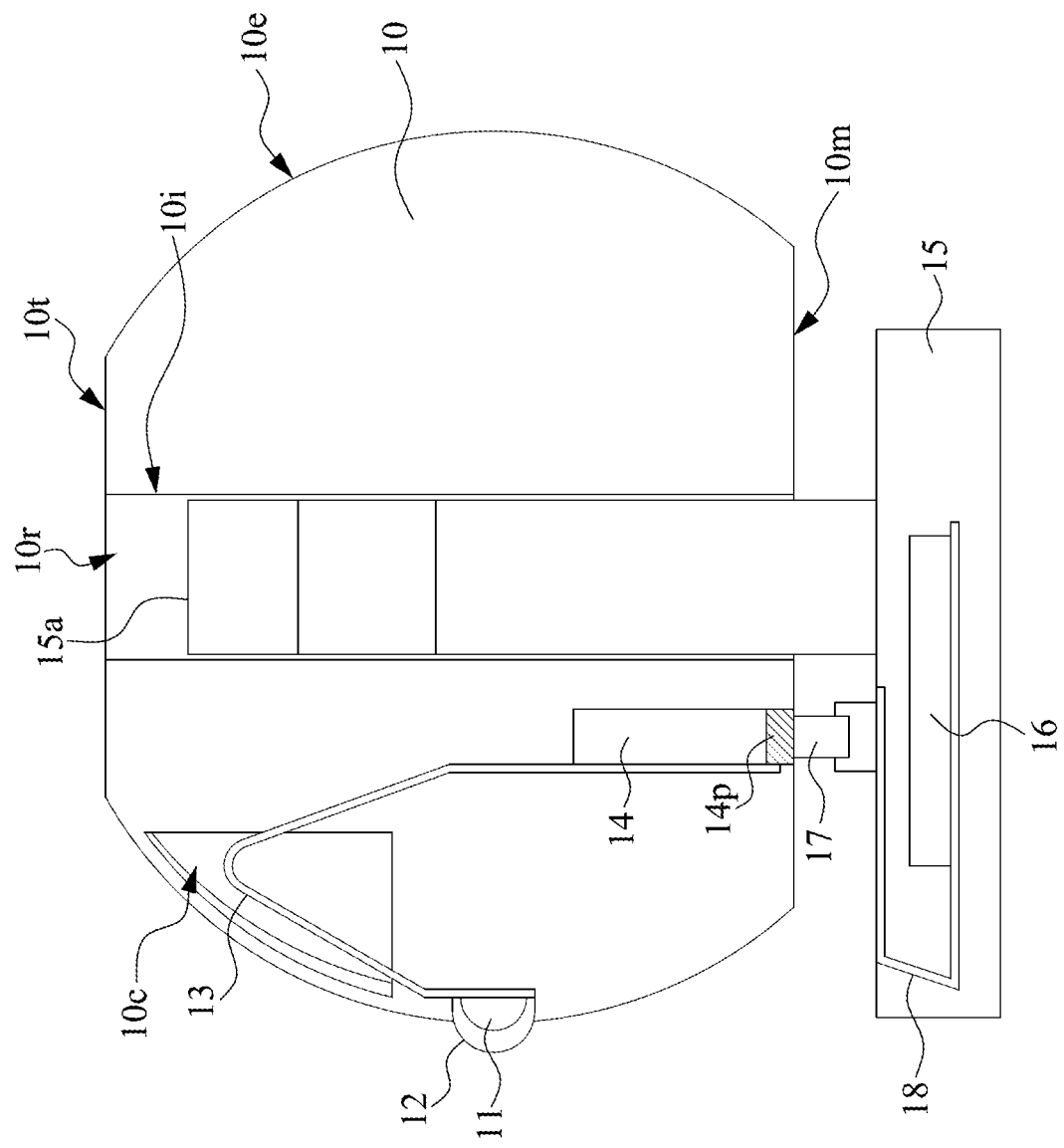
FIG. 1C illustrates a cross-sectional view of an electronic device in accordance with some embodiments of the present disclosure.

FIG. 1C illustrates a cross-sectional view of an electronic device in accordance with some embodiments of the present disclosure. In some embodiments, the electronic device 1 in FIG. 1A may be a part of the electronic device in FIG. 1C.

As shown in FIG. 1C, a piece of equipment 15 is partially adapted in the flexible element 10 from the bottom side 10m. In some embodiments, the piece of equipment 15 may be configured to transmit audio signals. For example, a sound hole 15a may be surrounded by the internal surface 10i of the flexible element 10. In some embodiments, the bottom side 10m may be shaped to receive the piece of equipment 15.

A conductive pad 17 may be at least partially exposed by the piece of equipment 15. The conductive pad 17 may be electrically connected with the conductive element 14p. When the piece of equipment 15 is partially adapted in the flexible element 10 from the bottom side 10m, the conductive pad 17 may face the bottom side 10m. For example, the conductive pad 17 may be arranged according to the conductive element 14p.

The conductive element 14p may be electrically connected to an electronic component 16 in the piece of equipment 15 through the conductive pad 17 and a connector 18.

In some embodiments, the electronic component 16 may be a chip or a die including a semiconductor substrate, one or more integrated circuit devices and one or more overlying interconnection structures therein. The integrated circuit devices may include active devices such as transistors and/or passive devices such resistors, capacitors, inductors, or a combination thereof. In some embodiments, the electronic component 16 may include a processor, such as a central processing unit. In some embodiments, the electronic component 16 may also be integrated into the flexible element 10. In some embodiments, the signal from the sensing element 11 can be processed (e.g., converted to a digital signal, amplified, stored, etc.) within the flexible element 10 by the active component 14, and then transmitted to the electronic component 16 for further signal processing. For example, the active component 14 may perform front-end process, and the electronic component 16 may perform back-end process such as data analysis, computing, or data transformation for further applications.

Figure 2A:
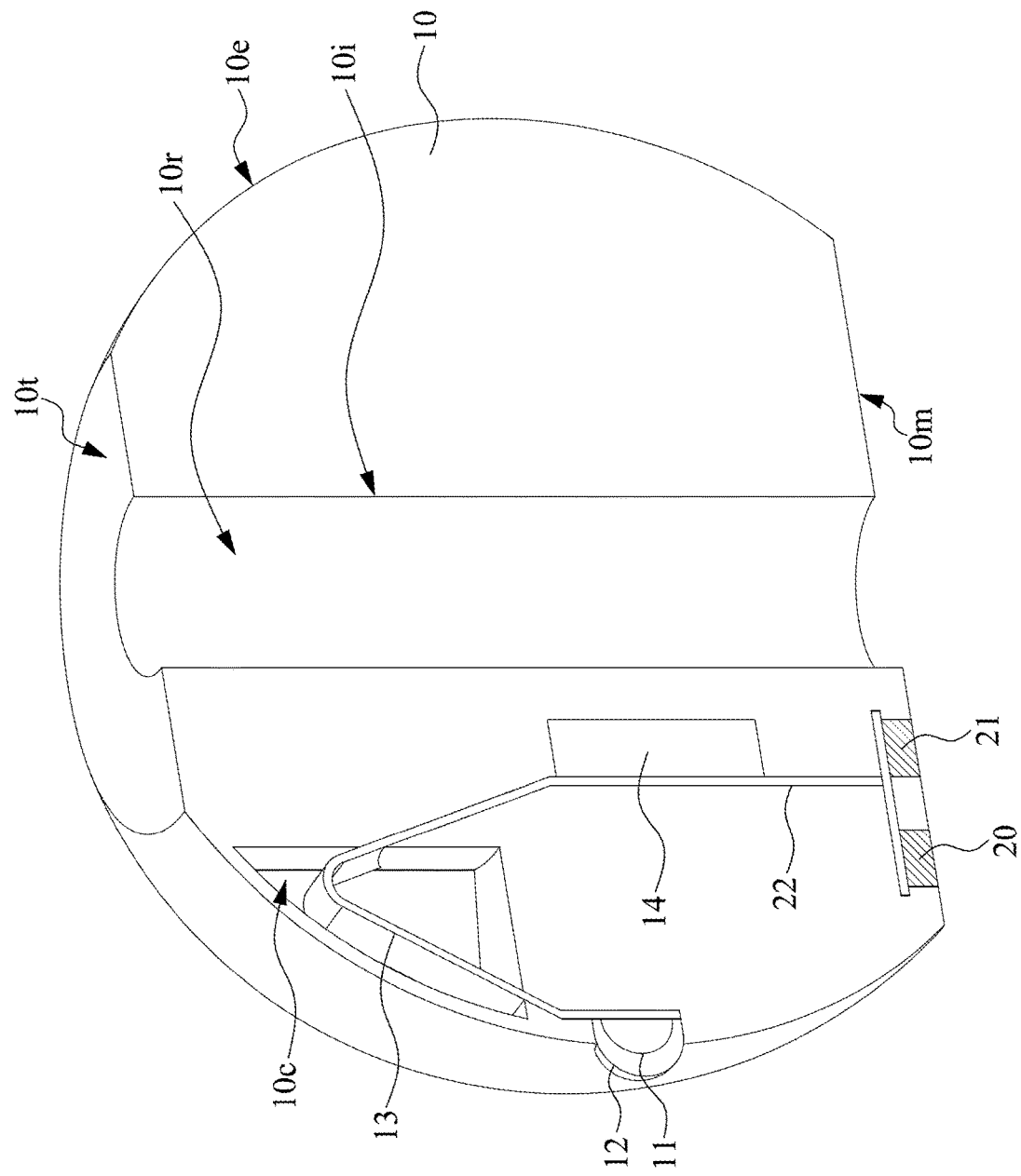
FIG. 2A illustrates a cross-sectional view of an electronic device in accordance with some embodiments of the present disclosure.

FIG. 2A illustrates a cross-sectional view of an electronic device 2 in accordance with some embodiments of the present disclosure. The electronic device 2 is similar to the electronic device 1 in FIG. 1A except for the differences described as follows.

As shown in FIG. 2A, the electronic device 2 may have conductive elements 20 and 21. Both of the conductive elements 20 and 21 may be at least partially exposed by the bottom side 10m of the flexible element 10. The conductive element 20 may be spaced apart from the conductive element 21. Both of the conductive elements 20 and 21 may be spaced apart from the active component 14.

The active component 14 of the electronic device 2 may be disposed adjacent to the internal surface 10i of the flexible element 10 and may be electrically connected with the conductive elements 20 and 21 through a connector 22. In some embodiments, the connector 22 may include an FPC, a conductive wire, a RDL, or a combination thereof.

The positions, the functions, and the numbers of the conductive elements in the electronic device 2 are not intended to limit the present disclosure. For example, there may be any number of conductive elements in the electronic device 2 due to design requirements.

In some embodiments, the signal detected by the sensing element 11 may be transmitted through the connector 13 to the active component 14 for further signal processing. The processed signal may then be transmitted through the connector 22 to the conductive elements 20 and 21, and finally to an external device.

Figure 2B:
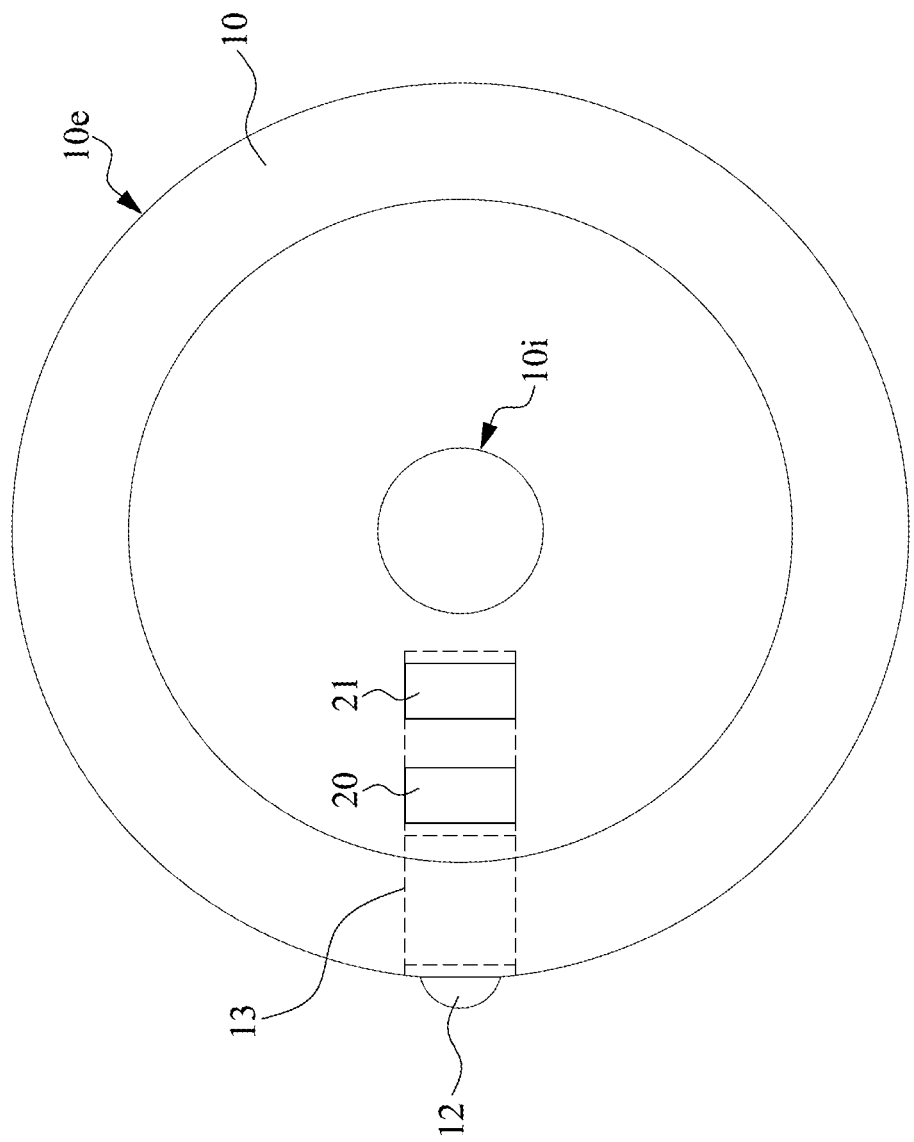
FIG. 2B illustrates a bottom view of an electronic device in accordance with some embodiments of the present disclosure.

FIG. 2B illustrates a bottom view of an electronic device in accordance with some embodiments of the present disclosure. In some embodiments, the bottom view in FIG. 2B may be a bottom view of the electronic device 2 in FIG. 2A. It should be noted that only the flexible element 10, the protection layer 12, the connector 13, and the conductive elements 20 and 21 are illustrated in FIG. 2B, and some components of the electronic device 2 in FIG. 2A are omitted for conciseness.

As shown in FIG. 2B, the conductive elements 20 and 21 are at least partially exposed by the bottom side 10m of the flexible element 10. The dashed line is illustrated to present a contour of the connector 13. From the bottom view, the connector 13 may be overlapped with the conductive elements 20 and 21.

Figure 2C:
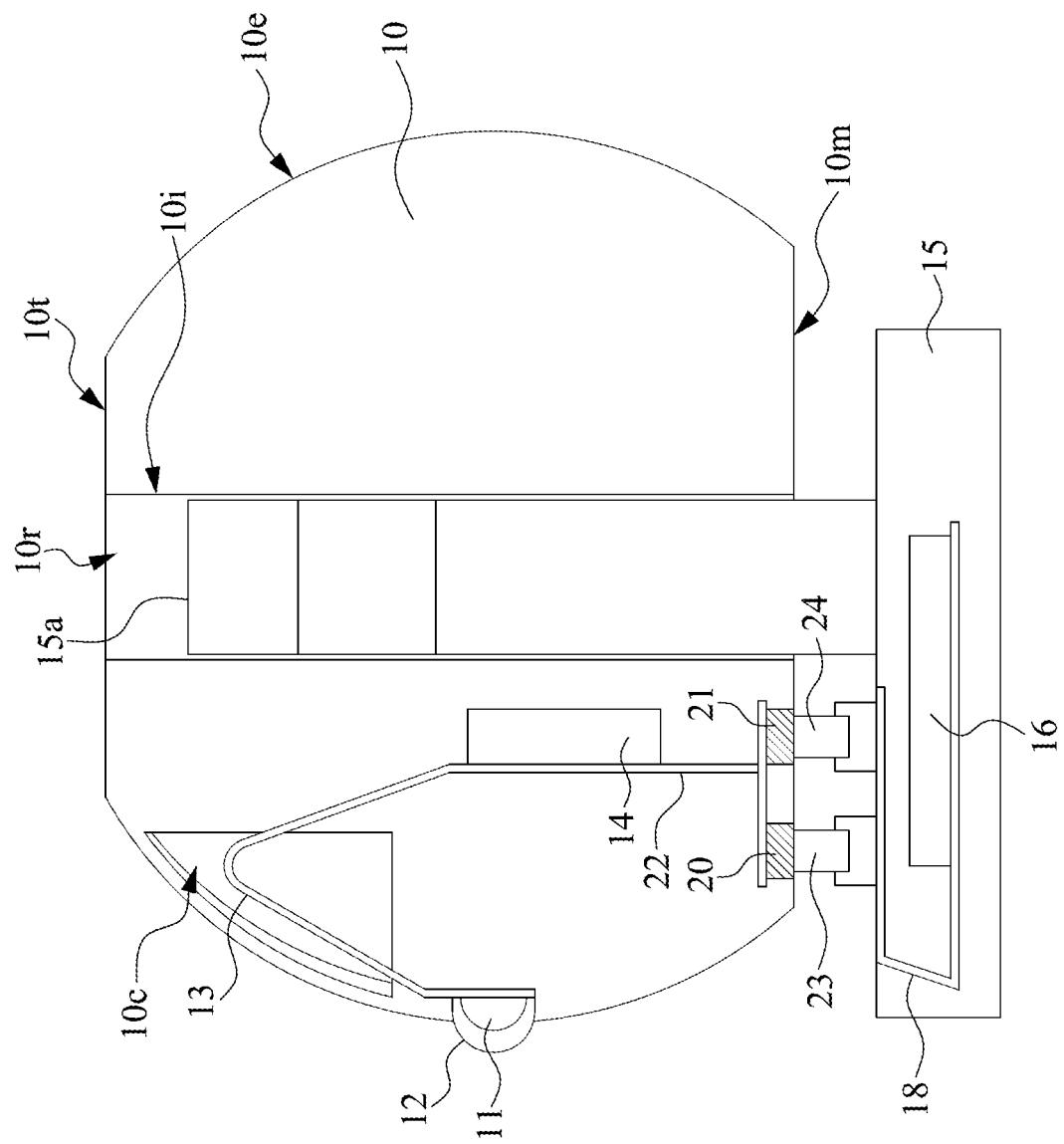
FIG. 2C illustrates a cross-sectional view of an electronic device in accordance with some embodiments of the present disclosure.

FIG. 2C illustrates a cross-sectional view of an electronic device in accordance with some embodiments of the present disclosure. In some embodiments, the electronic device 2 in FIG. 2A may be a part of the electronic device in FIG. 2C.

Conductive pads 23 and 24 may be at least partially exposed by the piece of equipment 15. The conductive pad 23 may be electrically connected with the conductive element 20. The conductive pad 24 may be electrically connected with the conductive element 21. When the piece of equipment 15 is partially adapted in the flexible element 10 from the bottom side 10m, the conductive pads 23 and 24 may face the bottom side 10m. For example, the conductive pads 23 and 24 may be arranged according to the conductive elements 20 and 21.

Figure 3A:
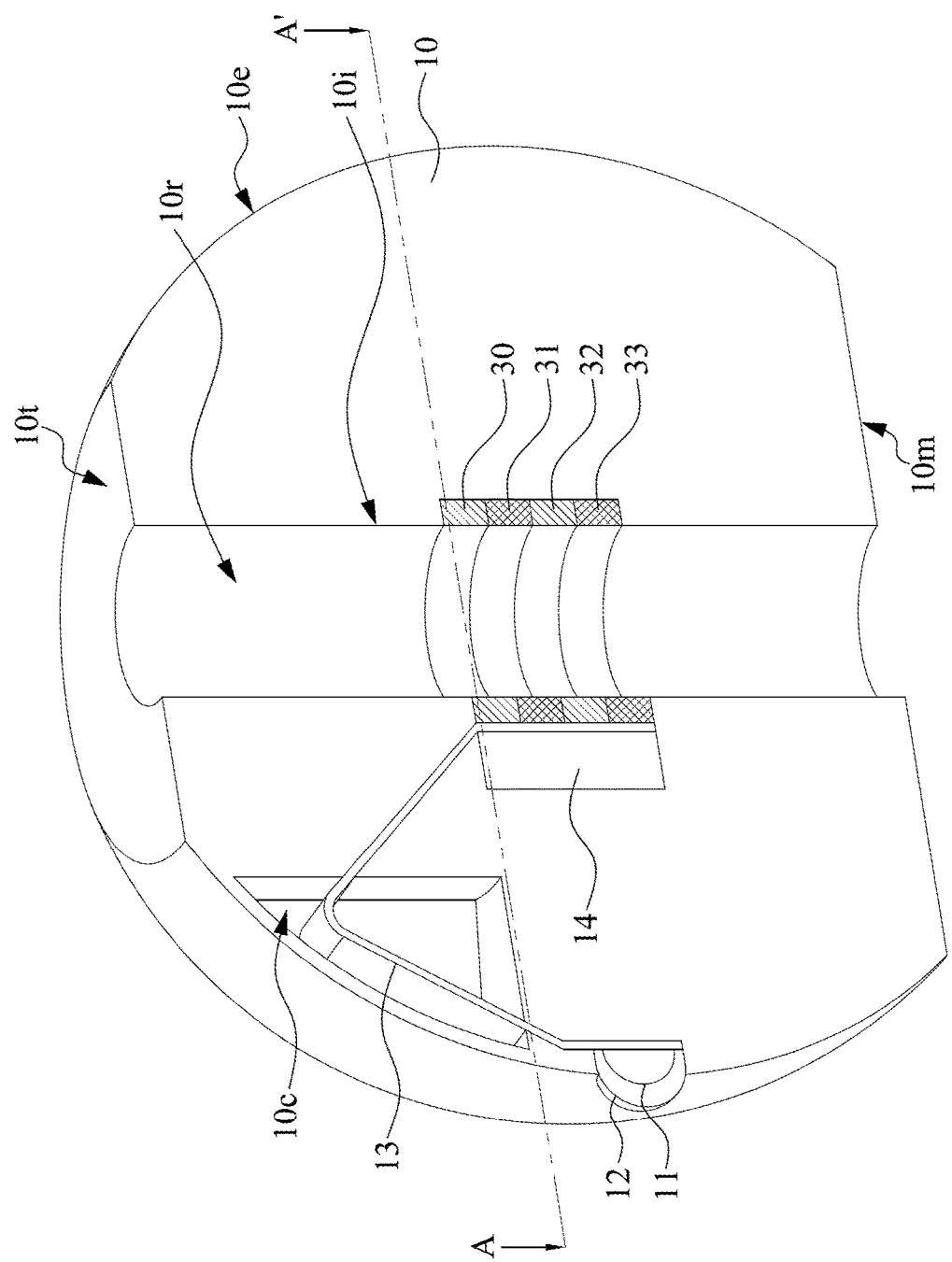
FIG. 3A illustrates a cross-sectional view of an electronic device in accordance with some embodiments of the present disclosure.

FIG. 3A illustrates a cross-sectional view of an electronic device 3 in accordance with some embodiments of the present disclosure. The electronic device 3 is similar to the electronic device 2 in FIG. 2A except for the differences described as follows.

The conductive elements 30 and 32 may be at least partially exposed by the internal surface 10i of the flexible element 10. In some embodiments, the conductive elements 30 and 32 may include one or more conductive pins of the active component 14. In some embodiments, the active component 14 may be electrically connected with the conductive elements 30 and 32 through a connector (not annotated in the figures). For example, the conductive elements 30 and 32 may be spaced apart from the active component 14 and may be electrically connected with the active component 14 through one or more connectors.

In some embodiments, the conductive elements 30 and 32 may have a curved surface. In some embodiments, a central angle defined by the conductive elements 30 and 32 may exceed 180°. For example, the conductive elements 30 and 32 may encircle or surround a central axis of the space 10r. In some embodiments, the conductive elements 30 and 32 may encircle or surround the internal surface 10i of the flexible element 10.

In some embodiments, the conductive element 30 may be spaced apart from the conductive element 32 by an insulating element 31. In some embodiments, the conductive element 32 may be spaced apart from the other conductive elements by an insulating element 33. In some embodiments, the insulating element 31 (and/or the insulating element 33) may have a curved surface. In some embodiments, a central angle defined by the insulating element 31 (and/or the insulating element 33) may exceed 180°. For example, the insulating element 31 (and/or the insulating element 33) may encircle or surround a central axis of the space 10r. In some embodiments, the insulating element 31 (and/or the insulating element 33) may encircle or surround the internal surface 10i of the flexible element 10. In some embodiments, the insulating element 31 and/or the insulating element 33 may be omitted.

In some embodiments, the signal detected by the sensing element 11 may be transmitted through the connector 13 to the active component 14 for further signal processing. The processed signal may then be transmitted (directly or through another connector) to the conductive elements 30 and 32, and finally to an external device.

Figure 3B:
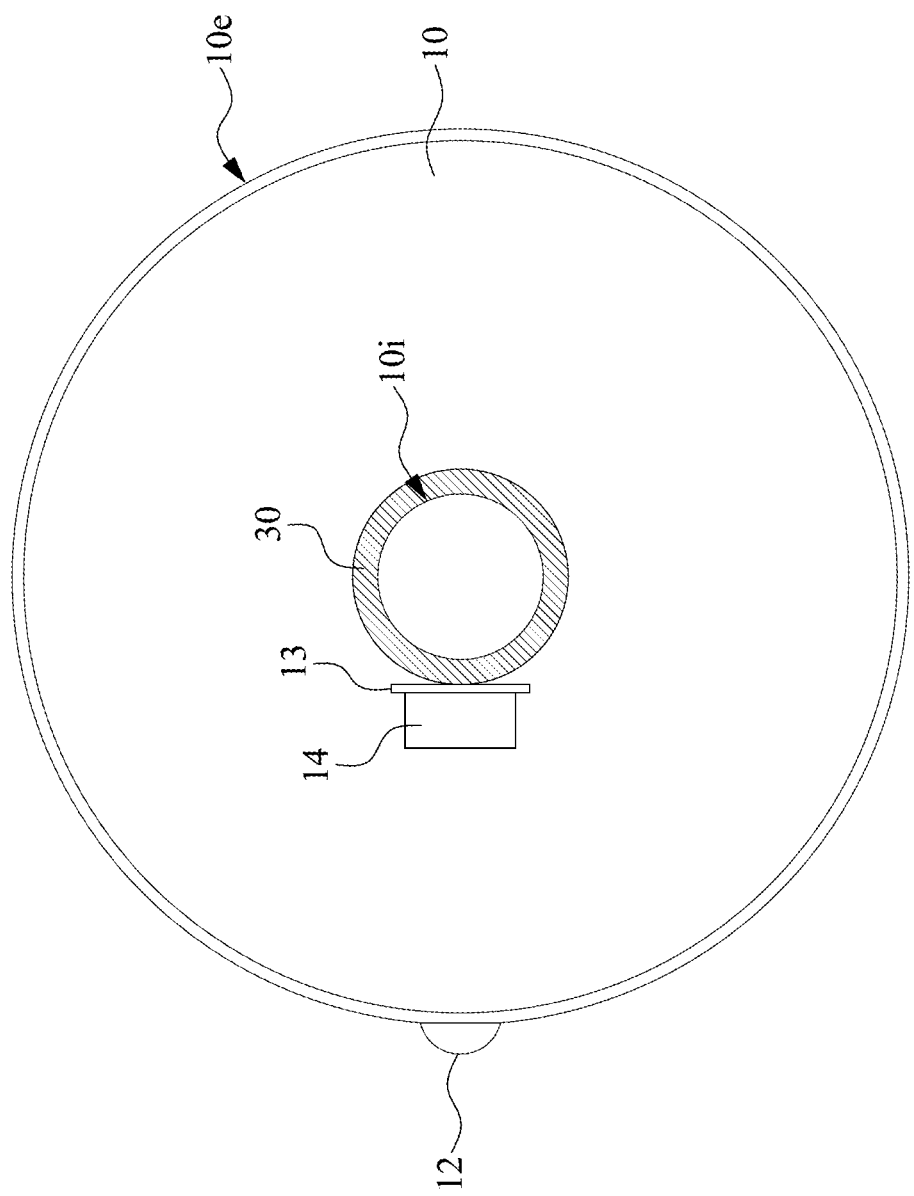
FIG. 3B illustrates a cross-sectional view of an electronic device in accordance with some embodiments of the present disclosure.

FIG. 3B illustrates a cross-sectional view of an electronic device in accordance with some embodiments of the present disclosure. In some embodiments, the cross-sectional view in FIG. 3B may be a cross-sectional view of the electronic device 3 in FIG. 3A along the line AA'. It should be noted that only the flexible element 10, the connector 13, and the conductive element 30 are illustrated in FIG. 2B, and some components of the electronic device 3 in FIG. 3A are omitted for conciseness.

As shown in FIG. 3B, the conductive element 30 may be at least partially exposed by the internal surface 10i of the flexible element 10. The insulating element 30 may circle or surround the internal surface 10i of the flexible element 10. The insulating element 30 may be annular.

Figure 3C:
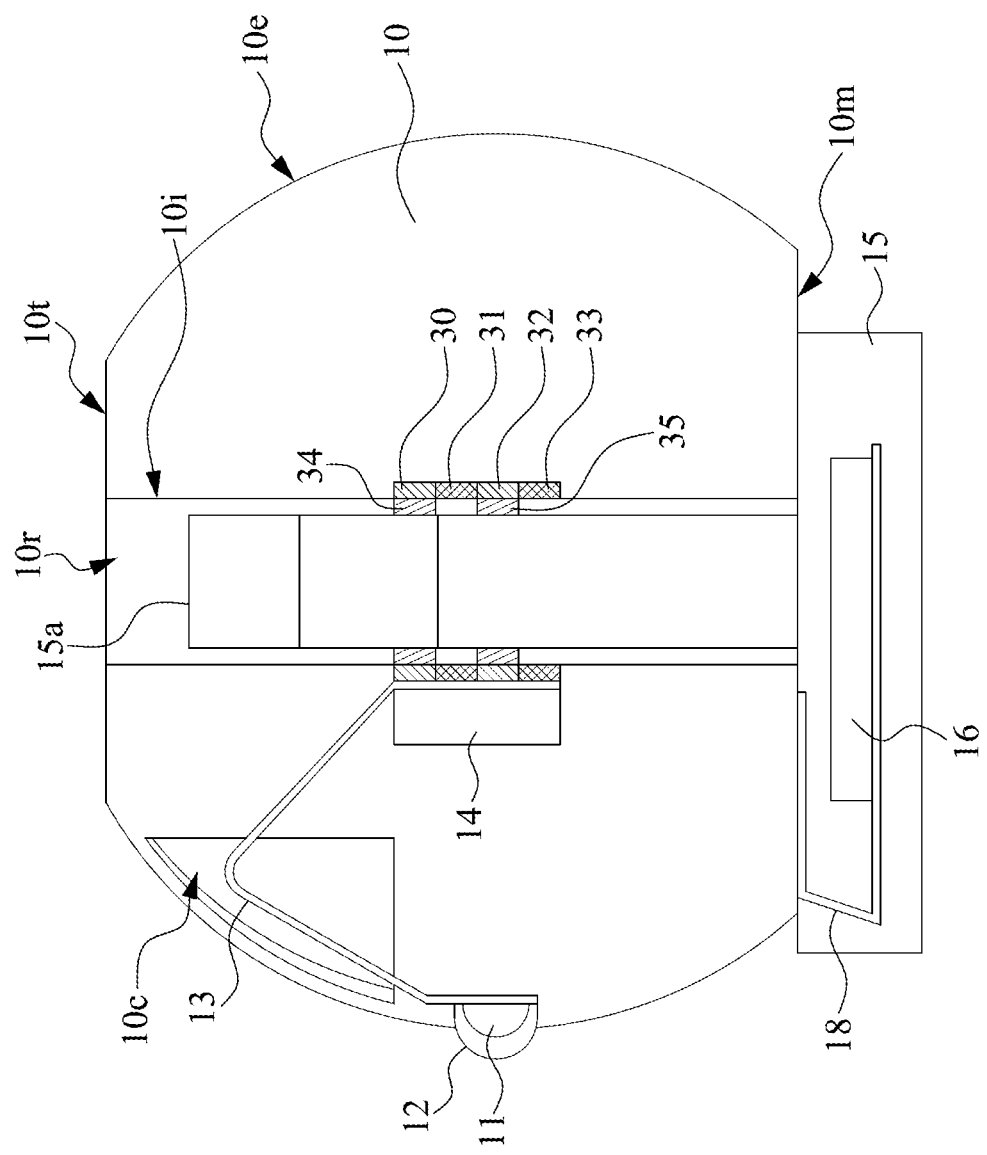
FIG. 3C illustrates a cross-sectional view of an electronic device in accordance with some embodiments of the present disclosure.

FIG. 3C illustrates a cross-sectional view of an electronic device in accordance with some embodiments of the present disclosure. In some embodiments, the electronic device 3 in FIG. 3A may be a part of the electronic device in FIG. 3C.

Conductive pads 34 and 35 may be arranged according to the conductive elements 30 and 32. For example, the conductive pad 34 may be electrically connected with the conductive element 30, and the conductive pad 35 may be electrically connected with the conductive element 32. When the piece of equipment 15 is partially adapted in the flexible element 10 from the bottom side 10m, the conductive pads 34 and 35 may face the internal surface 10i.

The conductive elements 30 and 32 may be electrically connected to the electronic component 16 in the piece of equipment 15 through the conductive pads 34 and 35 and the connector 18. In some embodiments, since the conductive elements 30 and 32 surround the internal surface 10i of the flexible element 10, the conductive pads 34 and 35 can be aligned with the conductive elements 30 and 32 without the risk of losing data if the piece of equipment 15 is rotated.

Figure 4A:
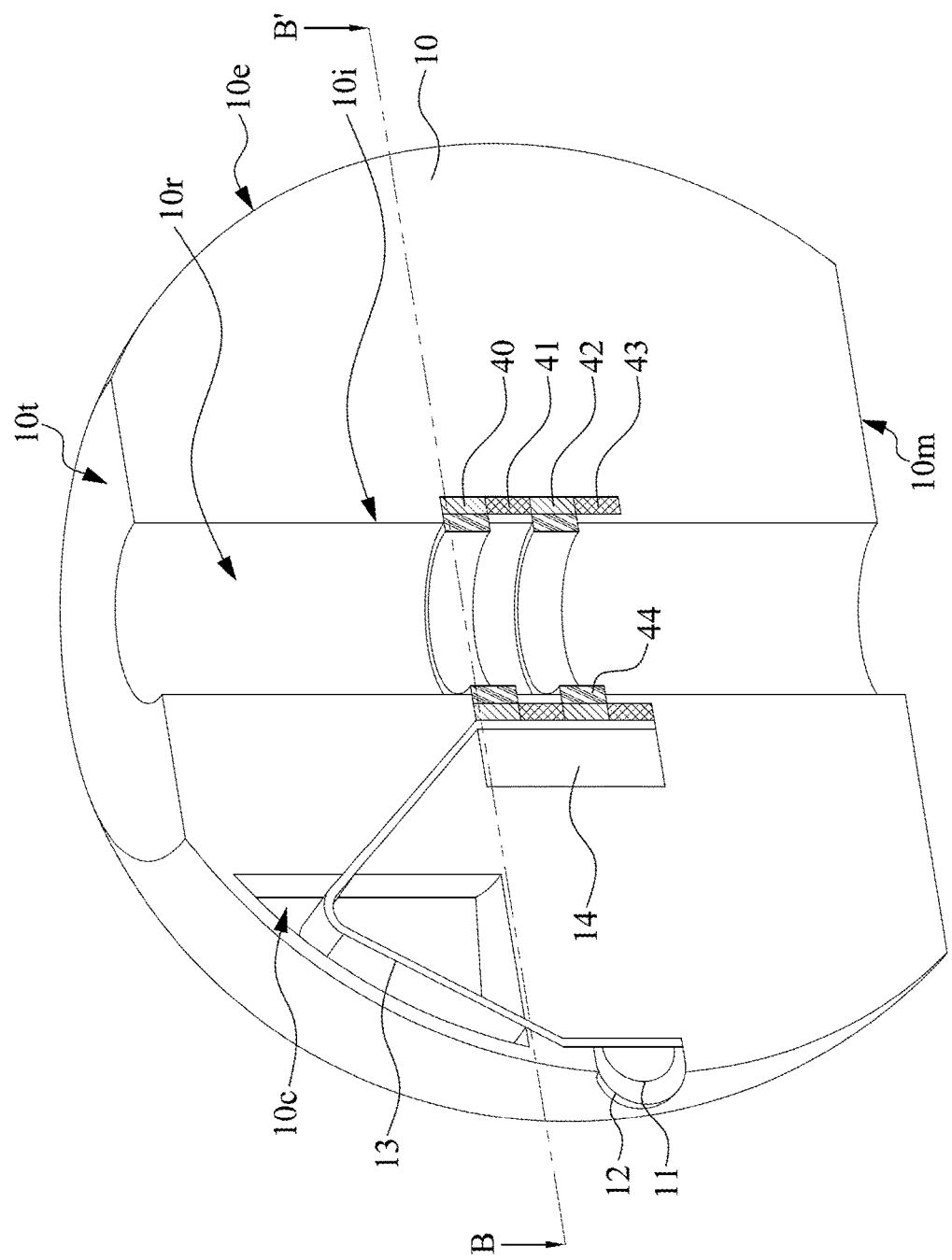
FIG. 4A illustrates a cross-sectional view of an electronic device in accordance with some embodiments of the present disclosure.
Figure 4B:
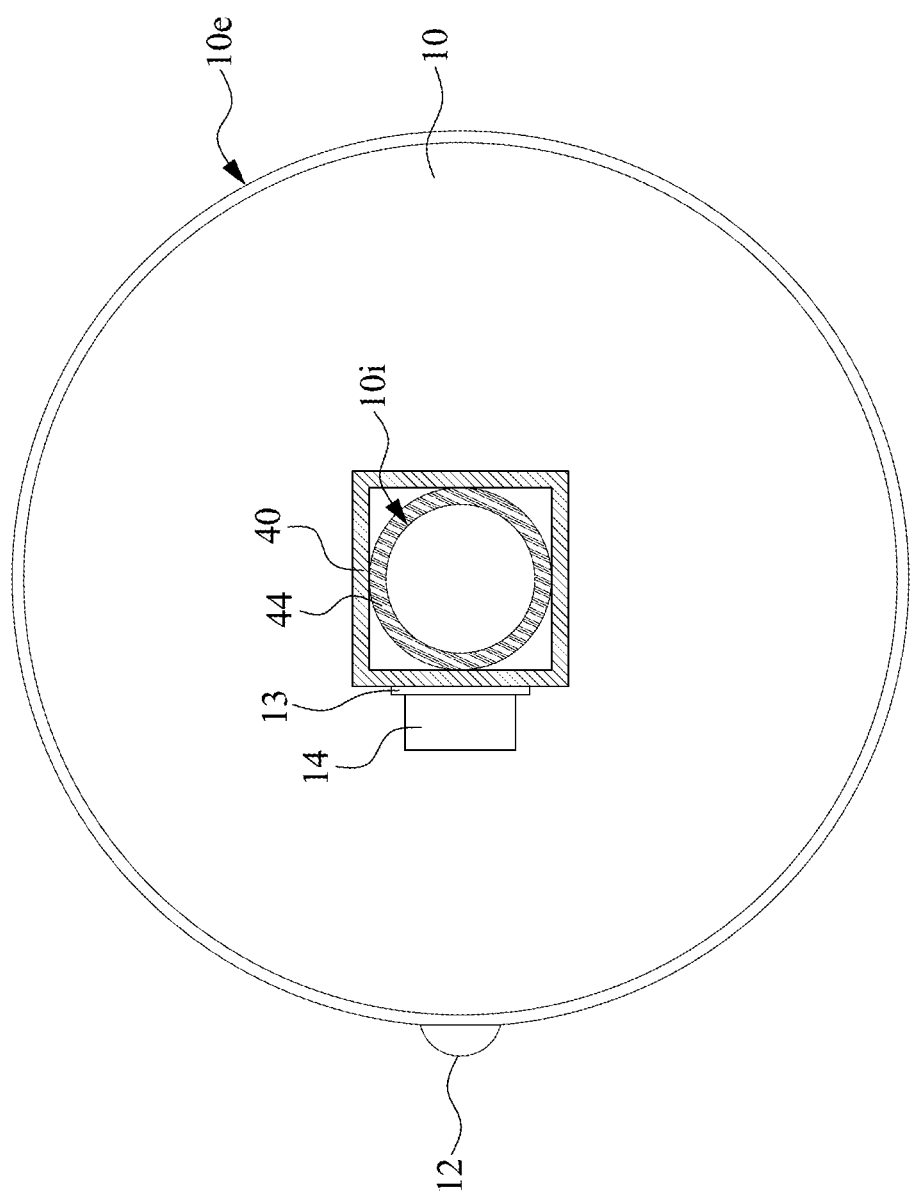
FIG. 4B illustrates a cross-sectional view of an electronic device in accordance with some embodiments of the present disclosure.
Figure 4C:
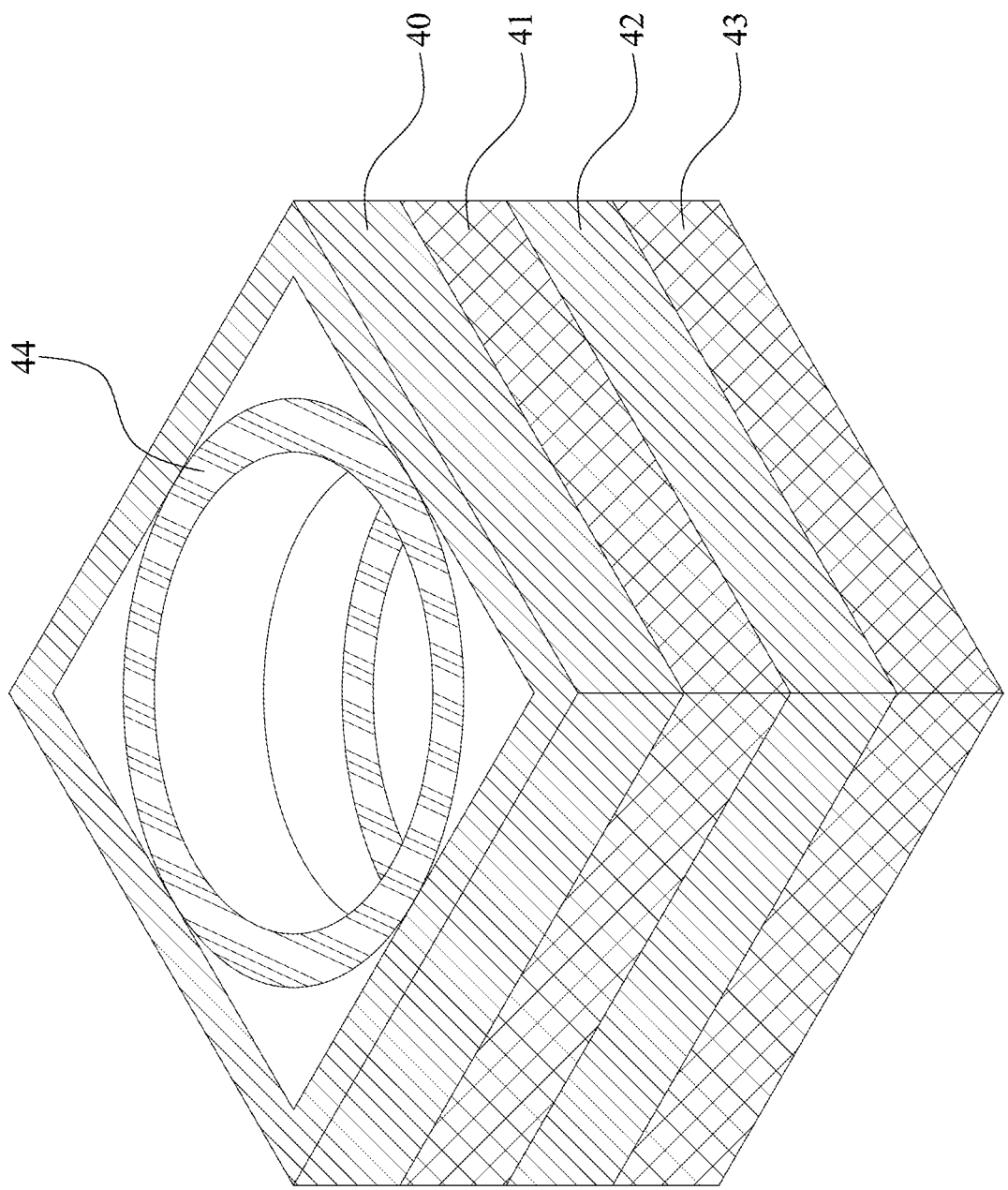
FIG. 4C illustrates a perspective view of a portion of an electronic device in accordance with some embodiments of the present disclosure.

FIG. 4A illustrates a cross-sectional view of an electronic device 4 in accordance with some embodiments of the present disclosure. FIG. 4B illustrates a cross-sectional view of an electronic device in accordance with some embodiments of the present disclosure. In some embodiments, the cross-sectional view in FIG. 4B may be a cross-sectional view of the electronic device 4 in FIG. 4A along the line BB'. FIG. 4C illustrates a perspective view of a portion of an electronic device in accordance with some embodiments of the present disclosure. In some embodiments, the perspective view in FIG. 4C may be a perspective view of a portion of the electronic device 4 in FIG. 4A. The electronic device 4 is similar to the electronic device 3 in FIG. 3A except for the differences described as follows.

Referring to FIG. 4B, the conductive element 40 may surround the internal surface 10i of the flexible element 10. The conductive element 40 may not be exposed by the internal surface 10i of the flexible element 10. The conductive element 40 may have a square or rectangular shape. The conductive element 40 may be square or rectangular. The conductive element 40 may be connected to the internal surface 10i of the flexible element 10 through a connector 44. A part of the flexible element 10 may be disposed between the conductive element 40 and the connector 44. The conductive element 40 may have a substantially planar surface. The active component 14 may have a surface corresponding to the conductive element 40.

In some embodiments, the electrical connection between the conductive element 40 and the active component 14 may be substantially planar, which provides better electrical conduction and more reliability.

The connector 44 may be at least partially exposed by the internal surface 10i of the flexible element 10. The connector 44 may have a curved surface. In some embodiments, a central angle defined by the connector 44 may exceed 180°. For example, the connector 44 may encircle or surround a central axis of the space 10r. In some embodiments, the connector 44 may encircle or surround the internal surface 10i of the flexible element 10. In some embodiments, the connector 44 may be annular.

Referring to FIG. 4C, in some embodiments, one or more insulating elements 41 and 43 may be formed along with the conductive elements 40 and 42.

Figure 4D:
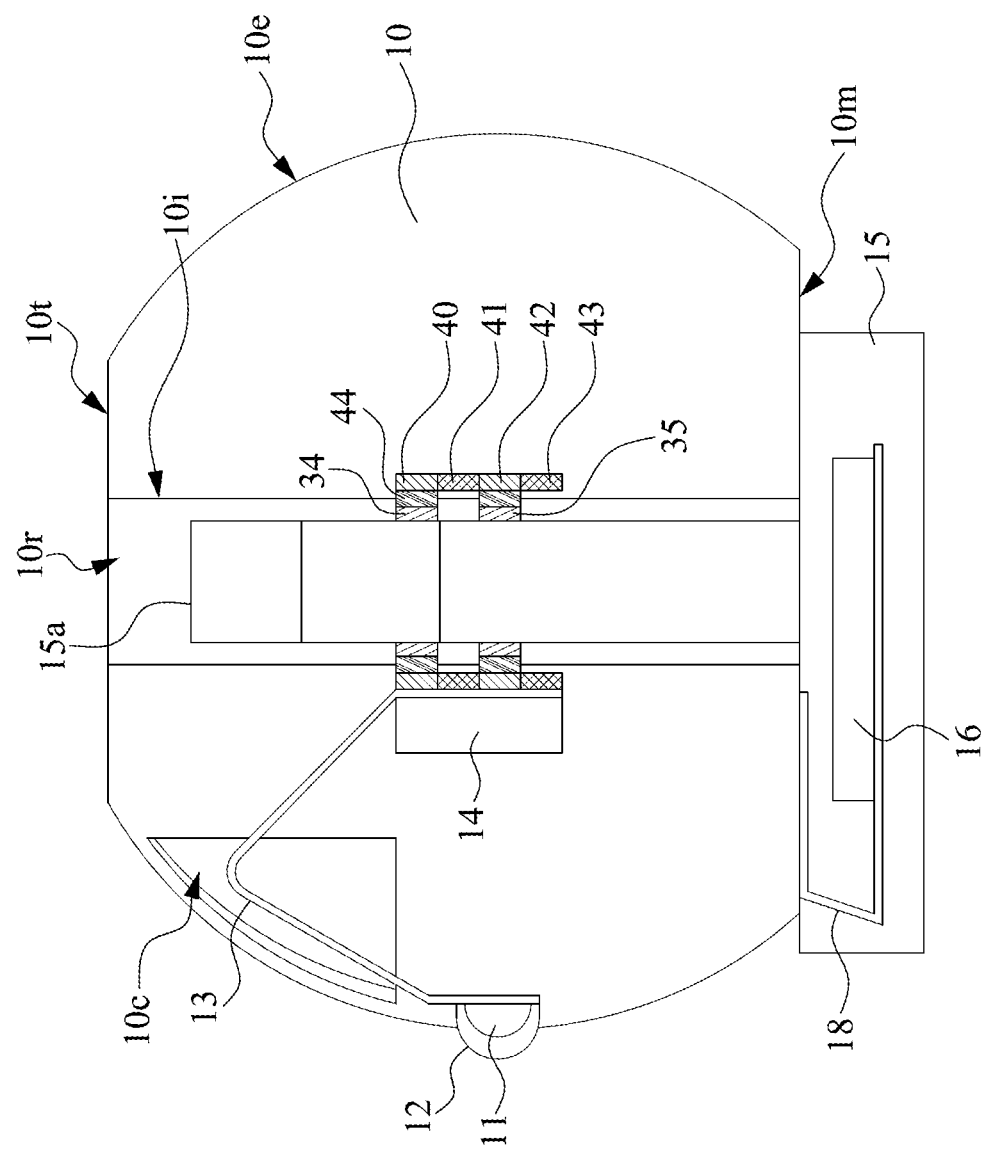
FIG. 4D illustrates a cross-sectional view of an electronic device in accordance with some embodiments of the present disclosure.

FIG. 4D illustrates a cross-sectional view of an electronic device in accordance with some embodiments of the present disclosure. In some embodiments, the electronic device 4 in FIG. 4A may be a part of the electronic device in FIG. 4D.

The conductive pads 34 and 35 may be arranged according to the conductive elements 30 and 32 (and the connectors 44). For example, the conductive pad 34 may be electrically connected with the conductive element 30 through the connectors 44, and the conductive pad 35 may be electrically connected with the conductive element 32 through the connectors 44. When the piece of equipment 15 is partially adapted in the flexible element 10 from the bottom side 10m, the conductive pads 34 and 35 may face the internal surface 10i.

The conductive elements 40 and 42 may be electrically connected to the electronic component 16 in the piece of equipment 15 through the connectors 44, the conductive pads 34 and 35 and the connector 18. In some embodiments, since the connectors 44 surround the internal surface 10i of the flexible element 10, the conductive pads 34 and 35 can be aligned with the connectors 44 without the risk of losing data if the piece of equipment 15 is rotated. In some embodiments, the connectors 44 and the conductive elements (such as the conductive elements 40 and 42) may be formed separately. In some embodiments, the connectors 44 and the conductive elements (such as the conductive elements 40 and 42) may be formed in one piece.

Figure 5A:
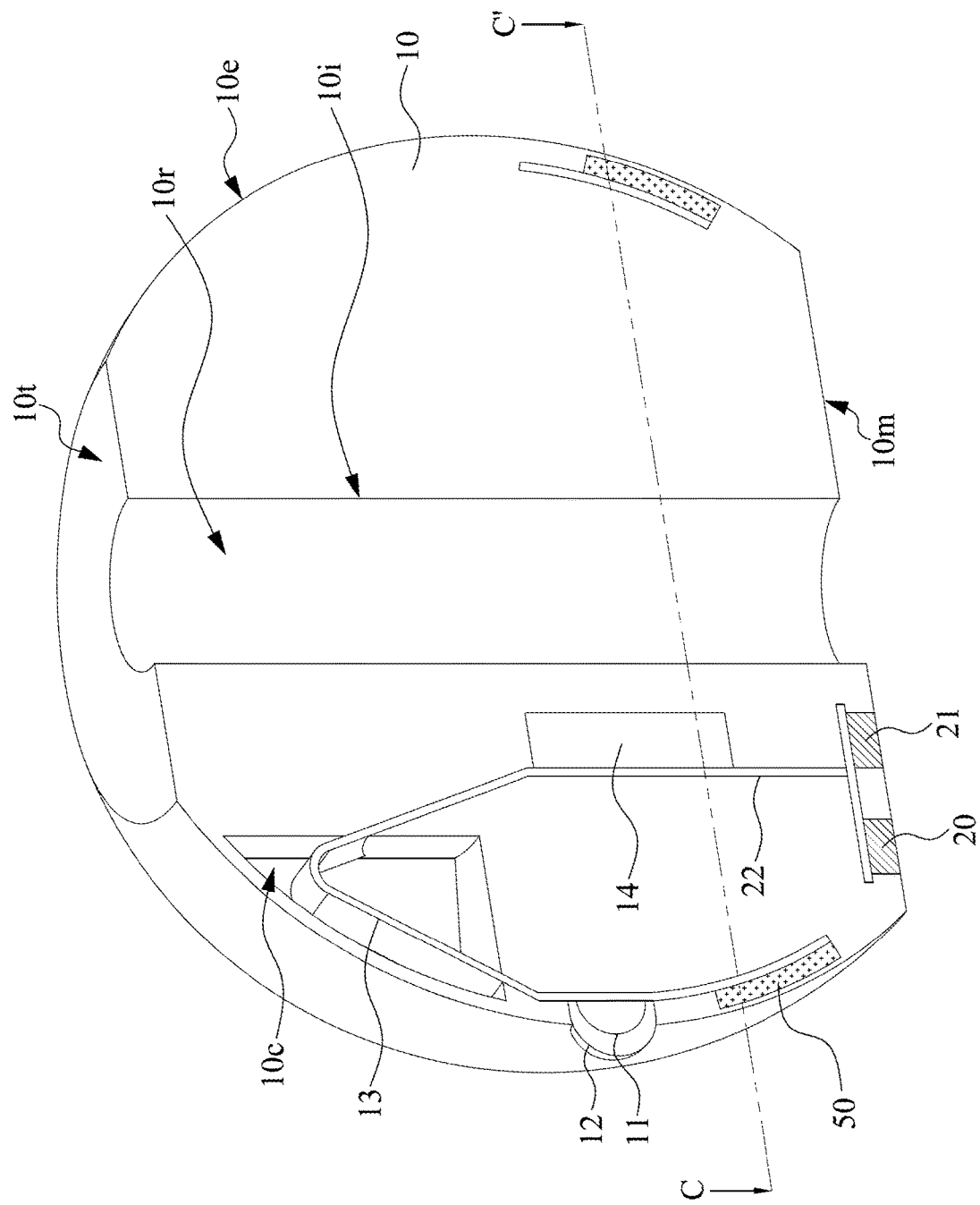
FIG. 5A illustrates a cross-sectional view of an electronic device in accordance with some embodiments of the present disclosure.
Figure 5B:
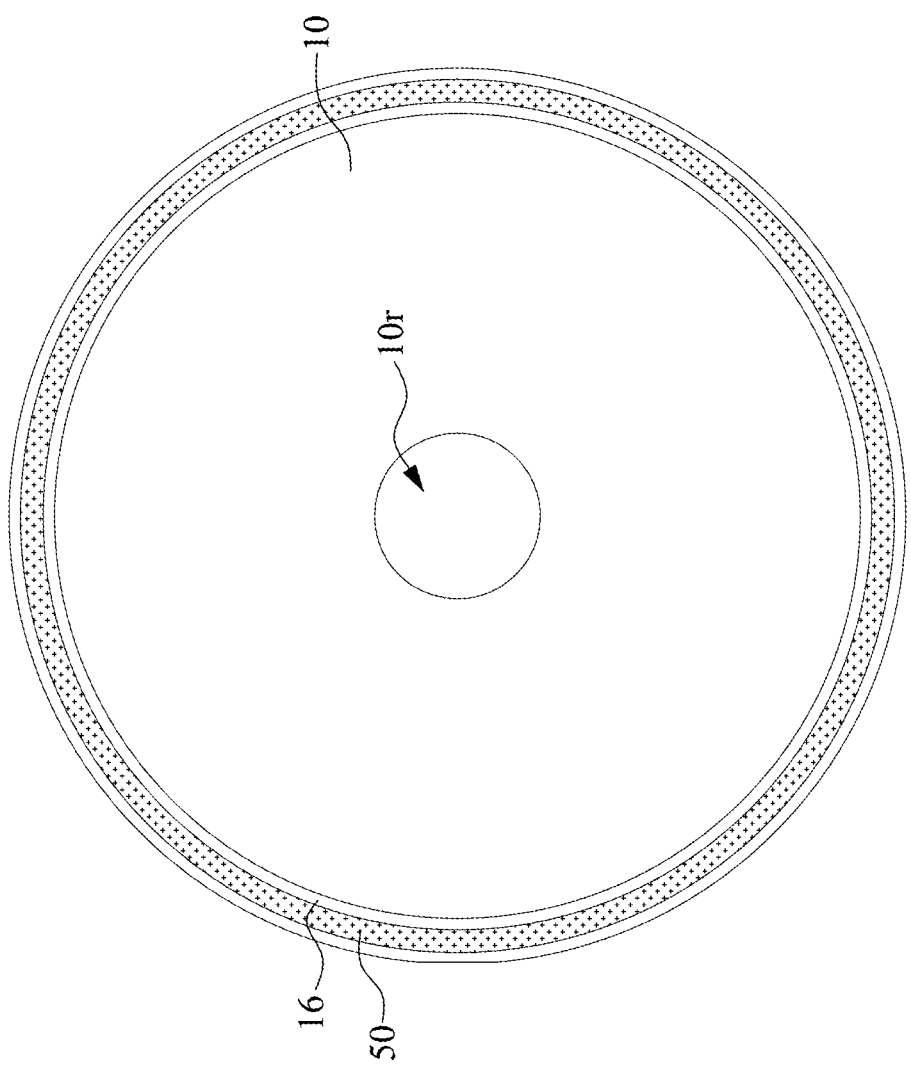
FIG. 5B illustrates a cross-sectional view of an electronic device in accordance with some embodiments of the present disclosure.

FIG. 5A illustrates a cross-sectional view of an electronic device 5 in accordance with some embodiments of the present disclosure. FIG. 5B illustrates a cross-sectional view of an electronic device in accordance with some embodiments of the present disclosure. In some embodiments, the cross-sectional view in FIG. 5B may be a cross-sectional view of the electronic device 5 in FIG. 5A along the line CC'. The electronic device 5 is similar to the electronic device 2 in FIG. 2A except for the differences described as follows.

The electronic device 5 further includes a sensing element 50. In some embodiments, the sensing element 50 may have a function or characteristic as listed previously for the sensing element 11. In some embodiments, the sensing element 50 may be an electrode used to detect ECG-relevant information. In some embodiments, the sensing element 50 may be disposed around the flexible element 10. In some embodiments, the sensing element 50 may circle or surround the flexible element 10 to increase the contact area with the user. For example, a central angle defined by the sensing element 50 may exceed 180°. For example, the sensing element 50 may encircle or surround a central axis of the space 10r. For example, from the cross-sectional view in FIG. 5B, the sensing element 50 may be annular. In some embodiments, the greater contact area with the user may help to collect more signals and improve the accuracy of the signals produced.

The sensing element 50 may be electrically connected to the active component 14 for signal transmission. For example, the sensing element 50 may be electrically connected to the active component 14 through the connector 13. In some embodiments, as shown in FIG. 5B, the connector 13 may circle or surround the flexible element 10. A central angle defined by the connector 13 may exceed 180°.

Figure 6:
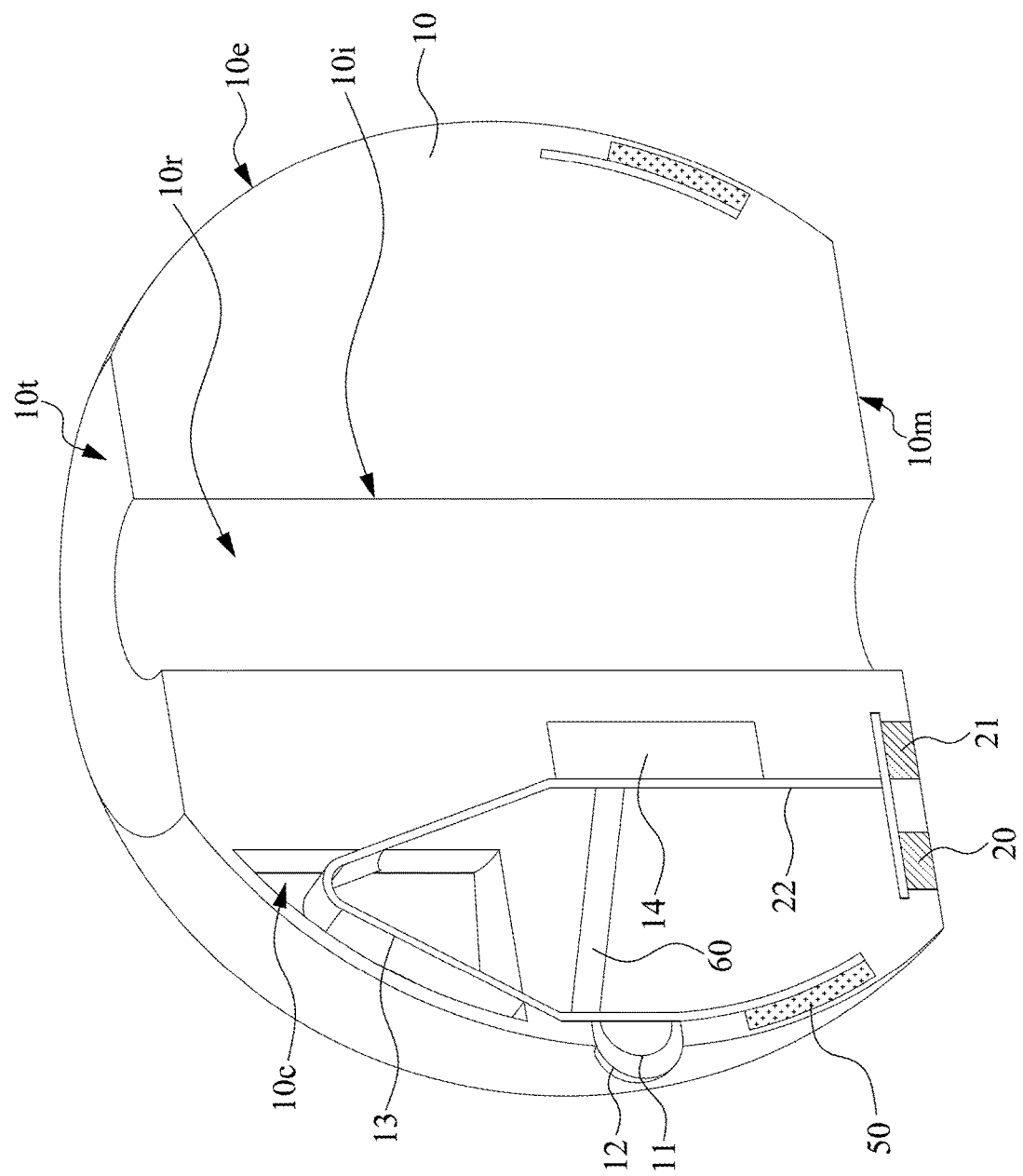
FIG. 6 illustrates a cross-sectional view of an electronic device in accordance with some embodiments of the present disclosure.

FIG. 6 illustrates a cross-sectional view of an electronic device 6 in accordance with some embodiments of the present disclosure. The electronic device 6 is similar to the electronic device 2 in FIG. 2A except for the differences described as follows.

The electronic device 6 further includes a supporting element 60 connected between the active component 14 and the sensing element 11. In some embodiments, the supporting element 60 may be flexible. In some embodiments, the electronic device 6 may include, for example, rubber, silicon, sponge, or other suitable materials such as an elastic material, a soft material, or a flexible material. In some embodiments, the supporting element 60 may include a spring or a wire bonding.

In some embodiments, the supporting element 60 may help the flexible element 10 to rebound and return to its original state. The connector 13 and the supporting element 60 may have different functions. The connector 13 may be used to provide signal transmission while the supporting element 60 may be used to improve the flexibility of the flexible element 10.

Figure 7:
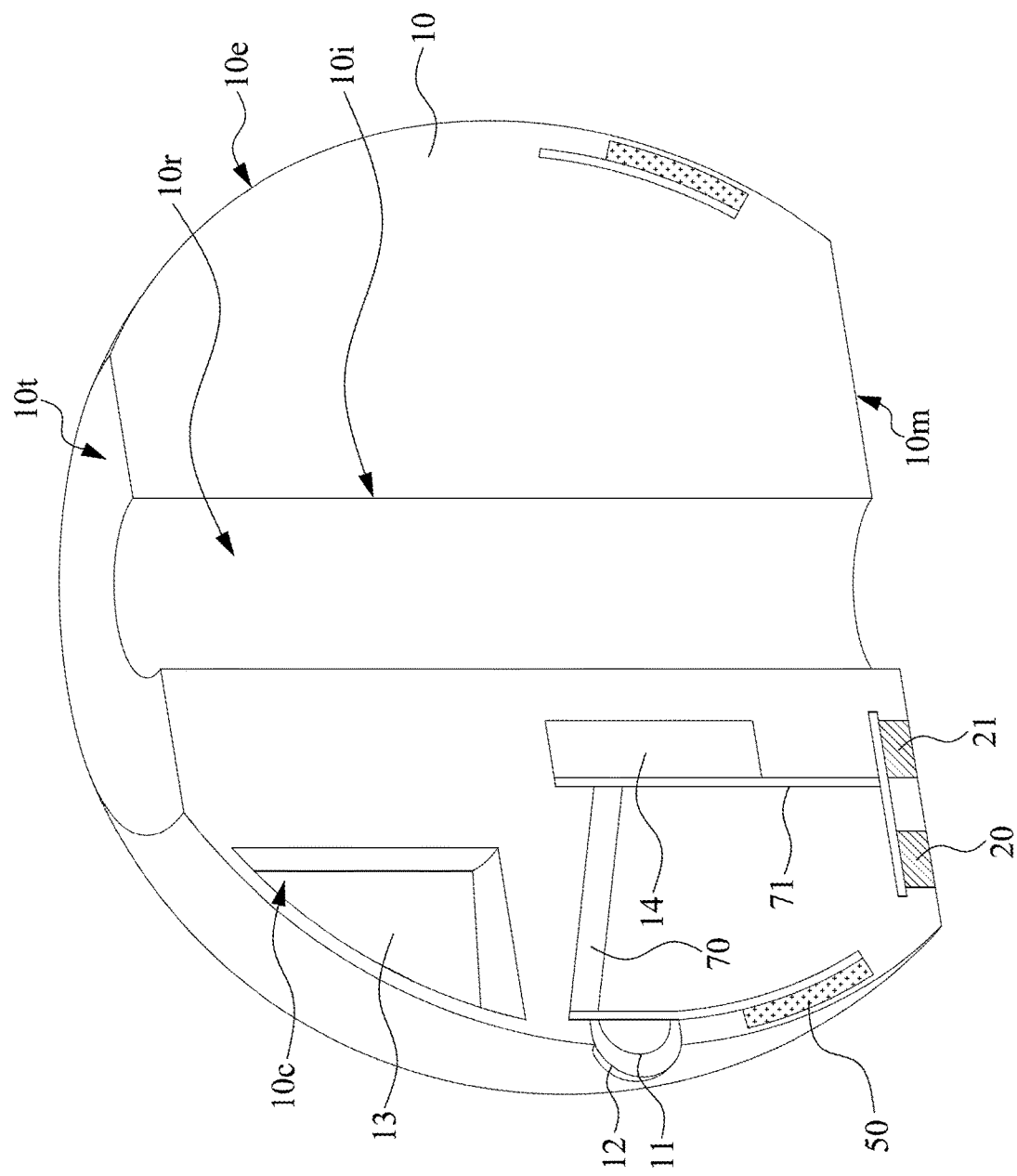
FIG. 7 illustrates a cross-sectional view of an electronic device in accordance with some embodiments of the present disclosure.

FIG. 7 illustrates a cross-sectional view of an electronic device 7 in accordance with some embodiments of the present disclosure. The electronic device 7 is similar to the electronic device 6 in FIG. 6 except for the differences described as follows.

The supporting element 70 of the electronic device 7 may be electrically conductive. The supporting element 70 may be electrically connected between the active component 14 and the sensing element 11 to provide signal transmission. Therefore, the connector 13 in FIG. 6 can be omitted. In some embodiments, the supporting element 70 may be further electrically connected with the conductive elements 20 and 21 through a connector 71.

As used herein, the singular terms "a," "an," and "the" may include a plurality of referents unless the context clearly dictates otherwise.

As used herein, the terms "conductive," "electrically conductive" and "electrical conductivity" refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately $10^4$ S/m, such as at least $10^5$ S/m or at least $10^6$ S/m. The electrical conductivity of a material can sometimes vary with temperature. Unless otherwise specified, the electrical conductivity of a material is measured at room temperature.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" parallel can refer to a range of angular variation relative to 0° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, "substantially" perpendicular can refer to a range of angular variation relative to 90° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. An electronic device, comprising:
   a flexible ear tip comprising a buffer portion which is not exposed by the flexible ear tip;
   a first sensing element adjacent to the flexible ear tip and configured to detect a biosignal through an ear canal of a user;
   an active component in the flexible ear tip and electrically connected with the first sensing element; and
   a connector disposed within the flexible ear tip and connecting the first sensing element and the active component,
   wherein the connector comprises a first portion within the flexible ear tip and a second portion within the buffer portion, and the first portion of the connector is not located within the buffer portion.

2. The electronic device of claim 1, wherein the connector comprises a third portion within the flexible ear tip, the first portion is connected to the active component, the second portion connects the first portion and the third portion, and the third portion connects the second portion and the first sensing element.

* * * * *